United States Patent [19]

Soeda et al.

[11] Patent Number: 6,030,821
[45] Date of Patent: *Feb. 29, 2000

[54] STABILIZED TRANSGLUTAMINASE AND ENZYME PREPARATION CONTAINING THE SAME

[75] Inventors: Takahiko Soeda; Keiko Hondo; Chiho Kuhara, all of Kawasaki, Japan

[73] Assignee: Ajinomoto Co., Inc., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/652,552

[22] PCT Filed: Oct. 11, 1995

[86] PCT No.: PCT/JP95/02076

§ 371 Date: Jul. 25, 1996

§ 102(e) Date: Jul. 25, 1996

[87] PCT Pub. No.: WO96/11264

PCT Pub. Date: Apr. 18, 1996

[30] Foreign Application Priority Data

Oct. 11, 1994 [JP] Japan ................................. 6-245211

[51] Int. Cl.$^7$ ........................................................ C12N 9/00
[52] U.S. Cl. .............................. 435/188; 435/193; 426/20
[58] Field of Search ............................. 435/193; 426/188, 426/20

[56] References Cited

U.S. PATENT DOCUMENTS

| | | | |
|---|---|---|---|
| 4,297,344 | 10/1981 | Scwinn et al. | 435/183 |
| 4,362,567 | 12/1982 | Schwarz et al. | 435/183 |
| 4,600,574 | 7/1986 | Lindner et al. | 435/183 |
| 4,917,904 | 4/1990 | Wakameda et al. . | |
| 5,055,310 | 10/1991 | Nonaka et al. . | |
| 5,196,956 | 3/1993 | Motoki et al. . | |
| 5,518,742 | 5/1996 | Soeda et al. . | |

*Primary Examiner*—Leon B. Lankford, Jr.
*Attorney, Agent, or Firm*—Oblon, Spivak, McClelland, Maier & Neustadt, P.C.

[57] ABSTRACT

This invention relates to stabilized transglutaminase which is obtained by drying a solution containing transglutaminase and a protein material and to a transglutaminase enzyme preparation that contains the stabilized transglutaminase as an active ingredient, wherein a partial protein hydrolysate is preferred as the protein material.

11 Claims, No Drawings

STABILIZED TRANSGLUTAMINASE AND ENZYME PREPARATION CONTAINING THE SAME

TECHNICAL FIELD

This invention relates to a stable transglutaminase having excellent shelf life (as the case may be, transglutaminase is abbreviated as TGase hereinafter) and a transglutaminase enzyme preparation which contains it as an active ingredient.

BACKGROUND ART

Decreased enzyme activities are observable in many enzymes when stored for a prolonged period of time.

TGase is an enzyme whose enzyme activity is decreased in a marked degree due, mainly, to oxygen when stored for a prolonged period of time. In consequence, a process in which an organic acid, an inorganic acid, a polyphenol, a thiol compound, a sugar alcohol and the like are used as additives has been developed with the aim of improving shelf life of TGase (cf. Japanese Patent Application Kokai No. 4-207194). However, improvement of shelf life by these additives is not sufficient. Especially, when TGase is stored under severe conditions such as storage throughout the summer season after its production, it is necessary to provide a proper means such as the use of an oxygen scavenger or vacuum treatment of the packaging, but these means are also still unsatisfactory.

DISCLOSURE OF THE INVENTION

In view of the above, it therefore becomes an object of the present invention to provide a stabilized TGase which can be stored for a prolonged period of time at ordinary temperature without requiring oxygen scavenger, vacuum packaging and the like and a transglutaminase enzyme preparation which contains the same.

With the aim of achieving the aforementioned object, the inventors of the present invention have conducted intensive studies and found that treatment of TGase by a specified method using a specified substance can stabilize it markedly so that its enzyme activity does not decrease even after a prolonged period of storage at ordinary temperature, and have accomplished the present invention on the basis of such a finding.

Accordingly, the present invention relates to a stabilized TGase obtained by drying a solution containing TGase and a protein material and to an enzyme preparation which contains it as an active ingredient.

The following illustratively describes the present invention.

Origin of the TGase to be stabilized in the present invention is not particularly limited, with the proviso that it is an enzyme having TGase activity. Examples of such an enzyme include those which are originated from mammals such as guinea pig and the like (cf. Japanese Patent Publication No. 1-50382), microorganisms such as of the genera Streptoverticillium and the like (for example, see Japanese Patent Application Kokai No. 64-27471) and fishes such as codfish and the like (for example, see Nobuo Seki et al., *Japan Journal of Scientific Fisheries*, vol.56, p.125, 1990) and those which are obtained by recombinant DNA techniques making use of biotechnology (cf. Japanese Patent Application Kokai Nos. 1-300,889, 5-199,883 and 6-225,775). Of these enzymes, microbial TGase is desirable from the view point that it can be produced in a large scale and does not require calcium for the expression of its enzyme activity.

Purity of the TGase to be stabilized also has no particular limitation. That is, either crude product or high purity product obtained by purification can be stabilized.

Next, a protein material to be used as a stabilizing agent is described. This is the specified substance described in the foregoing.

Examples of such a protein material broadly include plant proteins such as wheat protein, soybean protein and the like, animal proteins such as milk protein, the albumen, plasma protein, gelatin, cheese whey protein and the like and partial hydrolysates thereof, which have no particular limitation. Thus, it should be noted that partial protein hydrolysates are also included in the protein material of the present invention. Of these protein materials, the partial protein hydrolysate is particularly preferred, because it can be handled easily due to its small changes in viscosity when dissolved and it has high ability to keep the enzyme activity of TGase. As a matter of course, two or more protein materials may be used in combination in the present invention.

The partial protein hydrolysate can be obtained in the usual way. That is, using papain, bromelain, trypsin or the like enzyme, hydrochloric acid or the like acid or sodium hydroxide or the like alkali as a partial hydrolysis agent, a protein material is partially hydrolyzed under usually used partial hydrolysis conditions. As a matter of course, commercially available partial hydrolysates may also be used. The degree of hydrolysis of the partial hydrolysate has no particular limitation, provided that it has the TGase stabilizing function. In addition, the partial protein hydrolysate to be used in the present invention may be not only a purified product but also a product partially contaminated with impurities such as amino acids formed during the protein hydrolysis, provided that it has the TGase stabilizing function.

Drying of a solution containing TGase and a protein material, namely stabilization of TGase by the aforementioned specified method using a protein material, may be effected for example by either method in which (1) a protein material is added during the production process of TGase or (2) a protein material as the stabilizing agent is added to the produced TGase powder in a solvent, followed by dispersion and mixing and subsequent drying.

Illustratively, in the case of the method (1) in which a protein material is added during the production process of TGase, a protein material as the stabilizing agent is added to an enzyme solution sterilized after completion of culturing for the production of TGase in a production process disclosed for example in Japanese Patent Application Kokai No. 64-27471 (corresponding U.S. Pat. No. 5,156,956), immediately or during its concentration step, subsequently drying the mixture. Of the two adding modes, the latter case in which a protein material is added to the enzyme solution after its concentration to a certain level is preferred, because the protein material can be dissolved easily. Particularly, wheat protein and the like can be dissolved and uniformed more easily when a TGase solution becomes viscous by its concentration to a certain level.

When the method (2) is employed, the produced TGase powder and a protein material are dispersed in a solvent and mixed. This case is a method in which a protein material as the stabilizing agent and TGase are uniformly mixed by dispersing or dissolving them in a solvent such as water, a buffer solution, ethanol or the like and then dried.

In both cases of the methods (1) and (2), it is not necessary to positively set a retention time after the addition of the protein material and before the drying, but it is desirable to set a retention time within such a period that the enzyme activity does not decrease.

In this connection, the drying can be effected by a usually used means such as drying under reduced pressure, freeze drying or the like which does not cause inactivation of TGase.

Next, amounts of the TGase and stabilizing agent to be used when TGase is stabilized by the present invention are described. In the stabilizing methods (1) and (2) described above, there is no difference when these amounts are expressed by converting them to dry basis. That is, when TGase has a specific activity of approximately from 0.1 to 10 units/mg, the protein material is used in an adding ratio of from 0.01 to 200 weight parts, preferably from 0.5 to 100 weight parts, per 1 weight part of the enzyme. When the amount of the protein material is less than 1 weight part, its function to protect TGase is so weak that stabilization of the enzyme cannot be achieved. On the other hand, when the amount exceeds 200 weight parts, its protection function can be obtained but the resulting stabilized TGase has such a low activity that it is not suitable for practical use in food due to low expression of the TGase function.

A point which should not be overlooked in relation to the present invention is that TGase cannot be stabilized when dry powder of TGase is simply mixed with dry powder of a protein material even if TGase and the protein material are used within the aforementioned range. Stabilization of TGase can be attained for the first time by drying a solution containing TGase and the protein material. By doing this, it seems that TGase is incorporated into the matrix of a protein material, particularly into the matrix of the protein material in liquid form in which crosslink bonding (to be described later) is formed by TGase, and, as the result, protected from oxygen in the air and stabilized.

The stabilized transglutaminase (dry form) obtained in this manner may be used or distributed as it is, or other components (dry form) may be added to the stabilized transglutaminase (dry form) obtained in this manner and used or distributed in the form of an enzyme preparation.

Though it varies depending on the use of the enzyme preparation of the present invention, the component to be added may be selected optionally from additives generally used in enzyme preparations or used in the prior art TGase enzyme preparation. As such additives, various protein materials may be used, including milk proteins such as powdered milk, casein, casein sodium, casein calcium and the like, as well as wheat protein, soybean protein and the like. In addition, lactose, sodium polyphosphate, polyphenol, organic acid salts such as citrate and the like may also be blended. Also can be blended are seasoning materials such as salt, pepper, sugar, sodium glutamate, sodium inosinate, sodium guanylate and the like and emulsifiers such as lecithin, monoglyceride and the like.

In this connection, the stabilized TGase content of the enzyme preparation of the present invention is generally from 0.1 to 99 weight parts, preferably from 1 to 90 weight parts, per 100 weight parts of of the preparation. The content if less than 0.1 weight part would bear no function as the enzyme even with considerably increased dose of the enzyme preparation and if exceeding 99 weight parts would pose a difficulty in handling the preparation, because its amount to be added to the food of interest would become extremely small.

In comparison with those which are not stabilized, the stabilized TGase of the present invention or an enzyme preparation containing the same shows markedly small degree of periodical decrease in the enzyme activity and maintains at least about 80% of the initial activity even after one year of its production, so that it can be used effectively in a broad range of applications which include modification and adhesion of dairy products such as ice cream, yogurt, cheese and the like, animal or fish paste products such as ham, sausage, boiled fish paste and the like and various types of meat such as beef, pork, chicken meat and the like, as well as of baked wheat products such as bread and the like and pastas such as spaghetti and the like. Such effects are obtained by the modification of protein and peptide contained in materials of these products through the formation of intramolecular or intermolecular crosslink bonding generated by the enzyme action of TGase.

Though the TGase obtained by the present invention or an enzyme preparation containing the same has markedly high stability and shows extremely small degree of periodical inactivation as described in the foregoing, the degree of periodical inactivation can be further reduced by preserving or distributing it in an oxygen impermeable container having low oxygen permeability. It is desirable that the material of such a container has an oxygen permeability of 100 ml/m$^2$·atm·24 hr or less, preferably 30 ml/m$^2$·atm·24 hr or less. Examples of the container which satisfies the above criteria include containers in the form of a bag, a bottle and other shapes made of aluminum foil, aluminum deposition film, a polyvinyl alcohol resin, a nylon resin, a polyvinylidene chloride resin and the like.

In this connection, the activity unit of TGase is measured and defined as follows. That is, the enzyme reaction is carried out using benzyloxycarbonyl-L-glutaminylglycine and hydroxylamine as substrates, the thus formed hydroxamic acid is allowed to form its iron complex in the presence of trichloroacetic acid and then absorbance at 525 nm is measured to determine the amount of hydroxamic acid using a calibration curve and calculate the enzyme activity (cf. aforementioned Japanese Patent Application Kokai No. 64-27471).

As it is universally known, TGase is an enzyme which catalyzes acyl rearrangement reaction of the γ-carboxyamide group of glutamine residues in peptide chains. When the ε-amino group of lysine residues in protein acts as an acyl receptor, TGase catalyzes formation of ε-(γ-Glu)-Lys crosslink bonding in or between the protein molecules. Making use of such a function of TGase, modification of protein or peptide can be made (cf. Use Examples 1 to 5 which will be described later). Also, when water functions as an acyl receptor, this enzyme promotes a reaction in which glutamine residue is deaminated and converted into glutamic acid residue.

As has been described in the foregoing, the present invention relates to a stabilized TGase obtained by drying a solution containing TGase and a protein material, preferably a partial protein hydrolysate, and to a transglutaminase enzyme preparation which contains such a stabilized TGase as an active ingredient. Since the thus stabilized TGase is protected from the reduction of its enzyme activity caused by oxidation, it has a great advantage in that it can be preserved stably for a prolonged period of time at ordinary temperature in an oxygen-containing atmosphere.

As a matter of course, it is evident that the stabilized TGase of the present invention and the transglutaminase enzyme preparation which contains the stabilized TGase as an active ingredient can be provided with more higher stability, not only by containing them in oxygen-impermeable containers as described in the foregoing but also by further adding an oxygen scavenger thereto or by employing vacuum packaging or nitrogen-filled packaging.

BEST MODE OF CARRYING OUT THE INVENTION

The following describes the present invention further in detail with reference to some examples. As a matter of course, the technical range of the present invention is not limited by these examples.

Inventive Example 1

Using a Hovert Mixer (manufactured by Bokusui), 1 kg of microbial TGase (specific activity, 1.0 unit/mg) prepared in accordance with the method of Example 1 disclosed in the aforementioned Japanese Patent Application Kokai No. 64-27,471 was thoroughly mixed with 1 kg of each of the protein materials shown in the following Table 1 or, for the sake of comparison, with 10 g of sodium citrate disclosed in the aforementioned Japanese Patent Application Kokai No. 4-207194 (control (2)), and the resulting mixture was added to 5 kg of water. After dissolving the components by mixing and allowing the resulting solution to stand at room temperature for about 30 minutes, TGase was treated by drying the solution under a reduced pressure. In each case, specific activity after the treatment was around 0.45 unit/mg.

The thus treated TGase was packed and sealed in a container made of an aluminum laminate film (PET 12 μ/PE 15 μ/Al 9 μ/PE 15 μ/L-LDPE 70 μ) and preserved at 24° C. for 1 year. Results of the measurement of activities of the preserved TGase samples are also shown in Table 1. In this case, a TGase sample which has been treated without adding protein material and the like stabilizing agents was also prepared to be used as a control (control (1)). Also, a powder mixture consisting of 1 kg of the same transglutaminase having a specific activity of 1.0 unit/mg and 1 kg of "Sun Lacto" was preserved under the same conditions to be used as a control (control (3)).

As shown in Table 1, it was confirmed that each of the TGase samples which have been subjected to the stabilization treatment of the present invention using a protein material as the stabilizing agent was stabilized with a significant effect, in comparison with the controls. Also, the protein material was significantly excellent even in comparison with sodium citrate usually used as a stabilizing agent. In addition to the above, stabilizing effect of the protein material was not found when used as a powder mixture.

TABLE 1

| Stabilizing agent | Residual activity after 1 year of storage at 24° C. (%) |
| --- | --- |
| No addition (control (1)) | 54.9 |
| Separated soybean protein "Ajipron S2", manufactured by Ajinomoto | 82.1 |
| Albumen "Albumen Powder", manufactured by Taiyo Kagaku | 80.7 |
| Casein sodium "Sun Lacto", manufactured by Taiyo Kagaku | 85.5 |
| Wheat gluten partial hydrolysate "Glupearl 30", manufactured by Katayama Kagaku | 91.5 |
| Milk protein partial hydrolysate "Unifix", manufactured by Shin Nippon Seiyaku | 89.8 |
| Sodium citrate (control (2)) | 71.3 |
| Dry mixture of TGase and "Sun Lacto" (control (3)) | 52.3 |

Inventive Example 2

A fermentation broth of TGase prepared in accordance with the method of Example 1 disclosed in the aforementioned Japanese Patent Application Kokai No. 64-27471 was filtered, the resulting filtrate was subjected to ethanol separation to obtain a precipitate (specific activity, 0.5 unit/mg) and then 1 weight part of each of the stabilizing agents shown in Table 2 was added to 1 solid weight part of the thus obtained precipitate and uniformly mixed using a mixer. This was then dried under a reduced pressure to obtain the stabilized TGase of the present invention. In each case, specific activity was around 1.5 unit/mg.

The thus treated TGase was packed and sealed in the same aluminum laminate film container of Inventive Example 1 and preserved at 24° C. for 1 year. Results of the measurement of activities of the preserved enzyme samples are also shown in Table 2. In this case, a TGase sample which has been treated without adding protein material as the stabilizing agent was also prepared to be used as a control.

As shown in Table 2, it was confirmed that each of the TGase samples which have been subjected to the stabilization treatment of the present invention was stabilized with a significant effect, in comparison with the control. The enzyme activity just after drying of each sample subjected to the treatment of the present invention is also shown in the same table, and the results also confirm that loss of the enzyme activity during the stabilization treatment of the enzyme can be reduced by adding the stabilizing agent.

TABLE 2

|  | Activity just after treatment (100 as control) | Residual activity after 1 year of storage at 24° C. (%) |
|---|---|---|
| No addition (control) | 100 | 53.5 |
| Separated soybean protein "Ajipron S2" mfd. by Ajinomoto | 102 | 85.3 |
| Albumen "Albumen Powder" mfd. by Taiyo Kagaku | 102 | 85.5 |
| Casein sodium "Sun Lacto" mfd. by Taiyo Kagaku | 103 | 87.5 |
| Wheat gluten partial hydrolysate "Glupearl 30" mfd. by Katayama Kagaku | 105 | 93.1 |
| Milk protein partial hydrolysate "Unifix" mfd. by Shin Nippon Seiyaku | 105 | 92.2 |
| Soybean protein partial hydrolysate "High Nyuto R" mfd. by Fuji Seiyu | 110 | 93.5 |
| Wheat gluten partial hydrolysate "Glutamine Peptide" mfd. by DMV Japan | 115 | 96.0 |
| Milk protein partial hydrolysate "Peptide C2500" mfd. by Morinaga Milk | 110 | 94.4 |
| Milk serum protein partial hydrolysate "Peptide MA-L" mfd. by Morinaga Milk | 107 | 93.3 |
| Casein partial hydrolysate "MPH955" mfd. by Nippon Protein | 111 | 94.8 |
| Whey protein partial hydrolysate "ALATAL821" mfd. by Nippon Protein | 109 | 92.9 |

From the stabilized transglutaminase samples of Inventive Example 2 which have been stored for one year after the preparation, the sample stabilized using a wheat protein partial hydrolysate ("Glutamine Peptide" manufactured by DMV Japan) was selected and added to various foods described below to evaluate enzymatic function of transglutaminase. In this case, the transglutaminase stabilized using "Glutamine Peptide" is used herein simply as a typical example, and it is a matter of course that transglutaminase samples prepared using other stabilizing agents than the "Glutamine Peptide" can also show similar function. When the stabilized TGase of the present invention or an enzyme preparation which contains the stabilized TGase as an active ingredient is allowed to act upon protein or peptide, $\epsilon$-($\gamma$-Glu)-Lys crosslink bonds are formed in or between protein or peptide molecules, thereby rendering possible modification of protein or peptide.

Use Example 1 (Meat sausage)

To 1,000 g of 3 mm square pork having a fat content of about 30% were added 20 g of salt and 450 g of ice water, followed by thorough mixing using a Stefan cutter. To this were further added 70 g of a soybean protein article ("Ajipron S2" manufactured by Ajinomoto), 5 g of polyphosphate, 10 g of a seasoning ("I-7" manufactured by Ajinomoto) and 10 g (15,000 units) of the aforementioned stabilized TGase, subsequently mixing the contents using a Stefan cutter until final temperature of the mixture became 10° C. or below. In this case, the amount of added TGase was 2.5 units per 1 g protein. The thus obtained meat paste was packed in a casing, subjected to 15 minutes of smoking at 80° C. in a smoke house and 45 minutes of boiling at 75° C. and then cooled to obtain a frankfurter.

As controls, two products were prepared by repeating the same procedure except that the aforementioned stabilized TGase was not added in one control and the aforementioned stabilized TGase was not added and the amount of ice water to be added was reduced to 250 g in the other control.

When the thus obtained three types of frankfurters were evaluated by comparing them organoleptically, the control in which 450 g of ice water was added but TGase was not used showed a poor touch to the teeth with no elasticity. Also, its shape as the final product became lean. However, when TGase was used, the product prepared using 450 g of ice water showed excellent quality, maintaining its elasticity and shape which were similar or superior to those of a product prepared using 250 g of ice water. Thus, the use of the stabilized TGase of the present invention has rendered possible further water thinning (increase in water addition ratio) while keeping the product quality in the production of sausages.

Use Example 2 (Ice cream)

A 200 g portion of milk was put into a 1 liter capacity container and warmed at 50° C. on a low fire, to which was subsequently added thoroughly loosened three egg yolks. To this was added 0.2 g the aforementioned stabilized TGase (1 unit per 1 g protein of the mixture), subsequently keeping the resulting mixture for 10 minutes. During this period, temperature of the mixture was controlled at 40 to 50° C. Next, 150 g of sugar and a table spoon-full of corn starch were added thereto and thoroughly mixed and then the mixture was heated on a low fire while thoroughly mixing until it becomes thick. Next, the bottom of the container was put into ice water and a few drops of vanilla essence was added while mixing the contents of the container. A 150 g portion of raw cream was added thereto and thoroughly mixed. Next, the thus obtained ice cream mix was transferred into a freezer and kept for 1 to 2 hours until its surface became solid, and then the entire portion was mixed. By repeating this step three times, an ice cream was obtained. In this case, for the sake of comparison, an ice cream (control product) was prepared by repeating the same process except that TGase was not added.

When the thus obtained two types of ice creams were organoleptically evaluated, the ice cream prepared in accordance with the present invention was excellent in spoon handling, smooth, strong in oily feeling and excellent in the taste and flavor. Also, its shape-keeping ability after 20 minutes of standing at room temperature was excellent in comparison with the control product, keeping its original shape almost completely though a slight stickiness was observed. These characteristic properties can be regarded as a result of the stabilization of milk protein emulsion effected by the action of TGase upon milk protein to form Glu-Lys bonding.

Use Example 3 (Yogurt)

A 1 kg portion of milk (fat-free solid content, 8.3%) was put into a 2 liter capacity beaker and mixed with the aforementioned stabilized TGase in a ratio of 1 unit per 1 g milk protein, and the mixture was stirred for 1 hour at 25° C. After 1 hour of standing, this was heated at 95° C. to inactivate transglutaminase. When the temperature reached 95° C., this was immediately cooled down to 44° C. and mixed with 1.5% per milk material of a commercial lactic acid bacterium starter "Joghurt V2" (manufactured by WIESY) to carry out about 4.5 hours of fermentation at the same temperature (inventive product). The thus obtained yogurt trial product showed a pH value of 4.65. For the sake of comparison, a yogurt sample was prepared for trial by repeating the same process except that the aforementioned stabilized TGase was not used (control product).

When each of these trial products was allowed to stand for 3 weeks in a refrigerator (about 15° C.), water separation ratio (weight ratio of separated milk serum to total yogurt) of the TGase-free control product reached 4.5%, but the TGase-added inventive product showed only 0.2% of the separation ratio, hardly showing water separation in appearance when observed by the naked eye, and the effect of TGase was still significant even when 40 days passed after its production.

According to an organoleptic evaluation carried out by 20 expert panelists 40 days after the production, the control product contained some raw granules and its eating touch was rough, while raw granules were not found in the inventive product which showed smooth eating touch inherent to yogurt. Similar to the aforementioned case, these characteristic properties can be regarded as a result of the stabilization of milk protein emulsification effected by the action of TGase upon milk protein to form Glu-Lys bonding.

Use Example 4 (Bread)

A 700 g portion of wheat flour (first grade hard flour) was mixed with 20 g of yeast, 1.3 g of yeast food and 380 g of water using a mixer, and the mixture was allowed to stand for 4 hours at 25° C. and at a humidity of 75% to effect primary fermentation, thereby obtaining a sponge dough. At the time of the completion of the fermentation, the dough showed a temperature of 28° C. and a pH value of 5.3. Using a mixer, this sponge dough was further kneaded with 300 g of other dough material (first grade semi-hard wheat flour), 20 g of salt, 30 g of sugar, 30 g of glucose, 30 g of shortening, 220 g of water and 0.2 unit per 1 g protein of the aforementioned stabilized TGase. After allowing to stand for about 10 minutes at the same temperature of the kneading, this was equally divided into 5 balls, allowed to stand for 10 minutes at 28° C. and then packed in a baking mold. This was again subjected to 50 minutes of fermentation at 37° C. and at a humidity of 85%. Thereafter, the thus fermented dough was put into an oven and baked at 220° C. for 40 minutes to prepare white bread (inventive product). As a control, another white bread was prepared by repeating the same process except that the aforementioned stabilized TGase was not used (control product).

The thus obtained two types of white bread samples were subjected to organoleptic evaluation in the following manner. That is, each of the white bread samples 4 days after the baking was cut in slices of 1.5 cm in thickness to carry out absolute organoleptic judgement by 10 panelists (5 males and 5 females) in terms of its texture, appearance, elasticity and eating touch, thereby finding that the inventive product was excellent in all of the evaluation items in comparison with those of the TGase-free control product.

Use Example 5 (Spaghetti)

A 2,000 g portion of durum semolina flour ("Leone B" manufactured by Nisshin Flour Milling) was mixed with 1 unit per 1 g flour protein of the aforementioned stabilized TGase and 600 g of city water, and the mixture was kneaded for 10 minutes and immediately subjected to an extrusion noodle making to obtain spaghetti cut to about 40 cm in length (inventive product). At the same time, another spaghetti was prepared by repeating the same process except that the aforementioned stabilized TGase was not used (control product).

Results of the evaluation of the thus obtained noodle samples showed that the TGase-added inventive product was excellent in hardness and elasticity, namely viscoelasticity, and organoleptically desirable, in comparison with the TGase-free control product.

Industrial Applicability

According to the present invention, a stabilized TGase which shows extremely low level of activity loss even after standing at ordinary temperature and a transglutaminase enzyme preparation which contains the former as an active ingredient can be obtained easily. These transglutaminase enzyme and enzyme preparation of the present invention can be stored at ordinary temperature for a prolonged period of time.

In addition, not only the stabilized TGase and enzyme preparation of the present invention can be used in the production of various foods such as sausage, ice cream, yogurt, bread, spaghetti and the like, but also proteins or peptides contained in raw materials of these foods can be modified by the use thereof and the quality of these foods can therefore be improved thereby.

We claim:

1. A method of preparing a composition used for food processing, comprising drying a solution comprising a microbial transglutaminase and an additional proteinaceous substance, to obtain a composition comprising the stabilized microbial transglutaminase, wherein the stabilized microbial transglutaminase retains at least 80% residual activity after one year of storage at 24° C.

2. The method of claim 1, wherein the proteinaceous substance is a plant protein, a milk protein, a cheese whey protein, a partial hydrosylate of a plant protein, a partial hydrosylate of a milk protein or a partial hydrosylate of a cheese whey protein.

3. A method of preparing a composition used for food processing, comprising drying a solution comprising a microbial transglutaminase and an additional proteinaceous substance selected from the group consisting of plant proteins, milk protein, albumen, plasma protein, cheese whey protein and partial hydrolysates thereof, to obtain a composition comprising the stabilized microbial transglutaminase.

4. The method of claim 3, wherein the proteinaceous substance is a plant protein, a milk protein, a cheese whey protein, a partial hydrosylate of a plant protein, a partial hydrosylate of a milk protein or a partial hydrosylate of a cheese whey protein.

5. A stabilized transglutaminase composition obtained by the method of claim 3.

6. A transglutaminase package in which the composition of claim 5 is packed and sealed in a container made of a material having an oxygen permeability of 100 ml/m²·atm·24 hr or less or subjected to vacuum packaging or nitrogen-filled packaging, together with an oxygen scavenger as occasion demands.

7. The composition of claim 5, wherein the composition is in freeze-dried form.

8. The composition of claim 5, wherein the proteinaceous compound is a partial protein hydrolysate.

9. The composition of claim 5, further comprising an additive agent.

10. The composition of claim 9, wherein the additive agent is selected from the group consisting of lactose, sodium polyphosphate, polyphenol, organic acid salts, and mixtures thereof.

11. A method for modifying proteins or peptides which comprises allowing the composition of claim 5 to act upon a protein or a peptide, thereby effecting formation of ε-(γ-Glu)-Lys crosslink bonding in or between molecules of the protein or peptide.

* * * * *